(12) United States Patent
Azizi et al.

(10) Patent No.: US 10,200,974 B2
(45) Date of Patent: Feb. 5, 2019

(54) METHODS AND ARRANGEMENTS TO MITIGATE COLLISIONS IN WIRELESS NETWORKS

(71) Applicant: Intel IP Corporation, Santa Clara, CA (US)

(72) Inventors: Shahrnaz Azizi, Cupertino, CA (US); Adrian P. Stephens, Cambridge (GB); Thomas J. Kenney, Portland, OR (US); Eldad Perahia, Portland, OR (US); Minyoung Park, Portland, OR (US)

(73) Assignee: Intel IP Corporation, Santa Clara, CA (US)

( * ) Notice: Subject to any disclaimer, the term of this patent is extended or adjusted under 35 U.S.C. 154(b) by 49 days.

(21) Appl. No.: 13/931,918

(22) Filed: Jun. 29, 2013

(65) Prior Publication Data

US 2014/0192820 A1 Jul. 10, 2014

Related U.S. Application Data

(60) Provisional application No. 61/750,335, filed on Jan. 8, 2013.

(51) Int. Cl.
*H04W 72/04* (2009.01)
*H04W 74/08* (2009.01)
(Continued)

(52) U.S. Cl.
CPC ............ *H04W 72/04* (2013.01); *C12N 15/74* (2013.01); *H04W 74/0816* (2013.01); *H04W 84/18* (2013.01)

(58) Field of Classification Search
CPC .............................. H04W 72/04; H04W 84/18
See application file for complete search history.

(56) References Cited

U.S. PATENT DOCUMENTS 8,411,807 B1 * 4/2013 Rangarajan ............ H04L 69/22
375/316
2009/0109943 A1 4/2009 Yomo et al.
(Continued)

FOREIGN PATENT DOCUMENTS

AU 2014205471 B2 2/2017
CN 104521161 A 4/2015
(Continued)

OTHER PUBLICATIONS

IEEE802.11ah working group specification, Proposed specification framework for TGah, doc: IEEE802.11-11/1137r12, Nov. 2012.*
(Continued)

*Primary Examiner* — Michael Thier
*Assistant Examiner* — Zhensheng Zhang
(74) *Attorney, Agent, or Firm* — Schwegman Lundberg & Woessner, P.A.

(57) ABSTRACT

Logic for collision mitigation between transmissions of wireless transmitters and receivers operating at different bandwidths. Logic of the receivers may be capable of receiving and detecting signals transmitted at narrower bandwidths. In several embodiments, the receivers comprise a clear channel assessment logic that implements a guard interval (or cyclic prefix) detector to detect transmissions at narrower bandwidths. For instance, a two MegaHertz (MHz) bandwidth receiver may implement a guard interval detector to detect 1 MHz bandwidth signals and a 16 MHz bandwidth receiver may implement logic to detect one or more 1 MHz bandwidth signals and any other combination of, e.g., 1, 2, 4, 8 MHz bandwidth signals. In many embodiments, the guard interval detector may be implemented to detect guard intervals on a channel designated as a primary channel as well as on one or more non-primary channels.

16 Claims, 6 Drawing Sheets

(51) Int. Cl.
  *C12N 15/74* (2006.01)
  *H04W 84/18* (2009.01)

(56) References Cited

U.S. PATENT DOCUMENTS

| | | | |
|---|---|---|---|
| 2009/0149127 A1 | 6/2009 | Viitamaki et al. | |
| 2010/0091716 A1* | 4/2010 | Bonta et al. | 370/329 |
| 2010/0118716 A1 | 5/2010 | Lakkis et al. | |
| 2011/0317674 A1 | 12/2011 | Park et al. | |
| 2012/0057534 A1 | 3/2012 | Park | |
| 2012/0263084 A1 | 10/2012 | Liu et al. | |
| 2012/0263086 A1* | 10/2012 | Liu et al. | 370/311 |
| 2012/0324315 A1 | 12/2012 | Zhang et al. | |
| 2012/0327870 A1 | 12/2012 | Grandhi et al. | |
| 2013/0107830 A1* | 5/2013 | Jones et al. | 370/329 |
| 2013/0176980 A1* | 7/2013 | Kneckt et al. | 370/329 |
| 2013/0195018 A1 | 8/2013 | Lv et al. | |
| 2015/0110051 A1 | 4/2015 | Azizi et al. | |

FOREIGN PATENT DOCUMENTS

| | | |
|---|---|---|
| JP | 2007067821 A | 3/2007 |
| RU | 2256293 C2 | 7/2005 |
| TW | 200805949 A1 | 1/2008 |
| TW | 201251382 A | 12/2012 |
| TW | 201434334 A | 9/2014 |
| TW | I521997 B | 2/2016 |
| TW | 201615051 A | 4/2016 |
| TW | I586191 | 6/2017 |
| WO | 2010045954 | 4/2010 |
| WO | WO-2010045019 A2 | 4/2010 |
| WO | 2012035196 | 3/2012 |
| WO | 2012055260 | 5/2012 |
| WO | WO-2012145404 A2 | 10/2012 |
| WO | WO-2014110188 A1 | 7/2014 |

OTHER PUBLICATIONS

"U.S. Appl. No. 14/578,660, Preliminary Amendment filed Dec. 23, 2014", 6 pgs.
"Australian Application Serial No. 2014205471, Amendment filed May 21, 2015", 11 pgs.
"Taiwanese Application Serial No. 103100500, Office Action dated Apr. 21, 2015", 9 pgs.
"Chinese Application Serial No. 201480000936.2, Voluntary Amendment dated Jul. 21, 2015", w/ English Claims, 9 pgs.
"International Application Serial No. PCT/US2014/010759, International Preliminary Report on Patentability dated Jul. 23, 2015", 13 pgs.
"Japanese Application Serial No. 2015-503695, Reasons of Rejection dated Aug. 11, 2015", w/ English Claims, 8 pgs.
"Korean Application Serial No. 2014-7027302, Office Action dated Sep. 9, 2015", w/ English Translation, 10 pgs.
"Taiwanese Application Serial No. 103100500,Response filed Jul. 20, 2015 to Office Action dated Apr. 21, 2015", w/ English Translation, 23 pgs.
"Australian Application Serial No. 2014205471, First Examiner Report dated Oct. 16, 2015", 4 pgs.
"Australian Application Serial No. 2014205471, Response to Sep. 28, 2016 to First Examiner Report dated Oct. 16, 2015", 19 pgs.
"Brazilian Application Serial No. 112014024067-1, Voluntary Amendment filed Jan. 14, 2016", not in English, 10 pgs.
"European Application Serial No. 14738152.9, Extended European Search Report dated Aug. 9, 2016", 7 pgs.
"Japanese Application Serial No. 2015-503695, Response filed Dec. 7, 2015 to Reasons of Rejection dated Aug. 11, 2015", w/ English Claims, 15 pgs.

"Korean Application Serial No. 2014-7027302, Notice of Preliminary Rejection dated Apr. 28, 2016", (English Translation), 5 pgs.
"Korean Application Serial No. 2014-7027302, Response filed Jan. 11, 2016 to Office Action dated Sep. 9, 2015", (English Translation of Claims), 31 pgs.
"Korean Application Serial No. 2014-7027302, Response filed Jun. 27, 2016 to Notice of Preliminary Rejection dated Apr. 28, 2016", w/ English Claims, 12 pgs.
"Russian Application Serial No. 2015121891, Office Action dated Mar. 16, 2016", Without English Translation, 9 pgs.
"Russian Application Serial No. 2015121891, Response filed Jun. 10, 2016 to Office Action dated Mar. 16, 2016", Without English Translation, 7 pgs.
"Taiwanese Application Serial No. 104139916, Office Action dated Aug. 22, 2016", w/ English Translation, 2 pgs.
Timo, Koskela, "802.11ah Channel Access Enhancement", IEEE 802.11-12/0877r2—date Jan. 16, 2012; Renesas Mobile Corporation, (Jul. 2012), 1-10.
U.S. Appl. No. 14/578,660, filed Dec. 22, 2014, Methods and Arrangements to Mitigate Collisions in Wireless Networks.
"Taiwanese Application Serial No. 104139916, Response filed Feb. 17, 2017 to Office Action dated Aug. 22, 2016", (W/ English Claims), 58 pgs.
"U.S. Appl. No. 14/578,660, Non Final Office Action dated Jan. 17, 2017", 10 pgs.
"Chinese Application Serial No. 201480000936.2, Office Action dated Feb. 16, 2017", w/ English Translation, 12 pgs.
"European Application Serial No. 14738152.9, Response filed Mar. 6, 2017 to Extended European Search Report dated Aug. 9, 2016", 16 pgs.
"Chinese Application Serial No. 201480000936.2, Response Filed Oct. 30, 2017 to Office Action dated Aug. 15, 2017", (W English Claims), 7 pgs.
"European Application Serial No. 14738152.9, Communication pursuant to Article 94(3) EPC dated Nov. 14, 2017", 5 pgs.
"Chinese Application Serial No. 201480000936.2, Office Action dated Jan. 22, 2018", 10 pgs.
"European Application Serial No. 14738152.9, Response Filed Mar. 2, 2018 to Communication pursuant to Article 94(3) EPC dated Nov. 14, 2017", 9 pgs.
"Chinese Application Serial No. 201480000936.2, Response filed Apr. 9, 2018 to Office Action dated Jan. 22, 2018", W O English Claims, 4 pgs.
"Chinese Application Serial No. 201480000936.2, Response filed Aug. 16, 2018 to Office Action dated Jun. 1, 2018", W English Claims, 60 pgs.
"European Application Serial No. 14738152.9, Response Filed Aug. 22, 2017 to Communication pursuant to Article 94(3) EPC dated Apr. 24, 2017", 11 pgs.
"Chinese Application Serial No. 201480000936.2, Office Action dated Aug. 15, 2017", 9 pgs.
"Chinese Application Serial No. 201480000936.2, Response Filed Jul. 3, 2017 to Office Action dated Feb. 16, 2017", (W English Claims), 11 pgs.
"U.S. Appl. No. 14/578,660, Final Office Action dated Jun. 27, 2017", 11 pgs.
"U.S. Appl. No. 14/578,660, Response filed May 17, 2017 to Non Final Office Action dated Jan. 17, 2017", 7 pgs.
"European Application Serial No. 14738152.9, Communication pursuant to Article 94(3) EPC dated Apr. 24, 2017", 6 pgs.
"European Application Serial No. 14738152.9, Communication Pursuant to Article 94(3) EPC dated Jun. 13, 2018", 4 pgs.
"Chinese Application Serial No. 201480000936.2, Office Action dated Jun. 1, 2018", W English translation, 15 pgs.
"Australian Application Serial No. 2017200698, First Examination Report dated Dec. 8, 2017", 3 pgs.
"Indian Application Serial No. 3012/CHENP/2015, First Examination Report mailed Aug. 21, 2018", W/ English Translation, 6 pgs.

\* cited by examiner

FIG. 1A

PHYSICAL LAYER PROTOCOL DATA UNIT 1060

| STF 1064 | LTF 1066 | 11AH-SIG 1068 | ADDITIONAL LTFS 1069 | DATA 1070 |

PREAMBLE STRUCTURE 1062

FIG. 1B

PHYSICAL LAYER PROTOCOL DATA UNIT 1080

| STF 1064 | LTF 1066 | 11AH-SIG 1068 | DATA 1070 |

PREAMBLE STRUCTURE 1082

FIG. 1C

11AH-SIG 1100

| MCS 1104 | BW 1106 | LENGTH 1108 | BF 1110 | STBC 1112 | CODING 1114 | AGGREGATION 1116 | SGI 1118 | CRC 1120 | TAIL 1122 |

METHODS AND ARRANGEMENTS TO MITIGATE COLLISIONS IN WIRELESS NETWORKS

TECHNICAL FIELD

Embodiments are in the field of wireless communications. More particularly, embodiments are in the field of collision mitigation between transmissions of wireless transmitters and receivers operating at different bandwidths.

BACKGROUND

In IEEE 802.11n/ac systems when double bandwidth was defined, half of the bandwidth was defined as primary channel and the other half as secondary channel. For example, a 40 MHz channel consists of primary 20 MHz and secondary 20 MHz channels. To enable coexistence of IEEE 802.11n/ac devices, standard specifications have defined Clear Channel Assessment (CCA) rules for both primary and secondary channels for the IEEE 802.11n/ac systems.

BRIEF DESCRIPTION OF THE DRAWINGS

FIG. 1A depicts an embodiment of a preamble for establishing communications between wireless communication devices;

FIG. 1B depicts an alternative embodiment of a preamble structure for establishing communications between wireless communication devices;

FIG. 1C depicts an embodiment of a signal field;

DETAILED DESCRIPTION OF EMBODIMENTS

Figure 1:
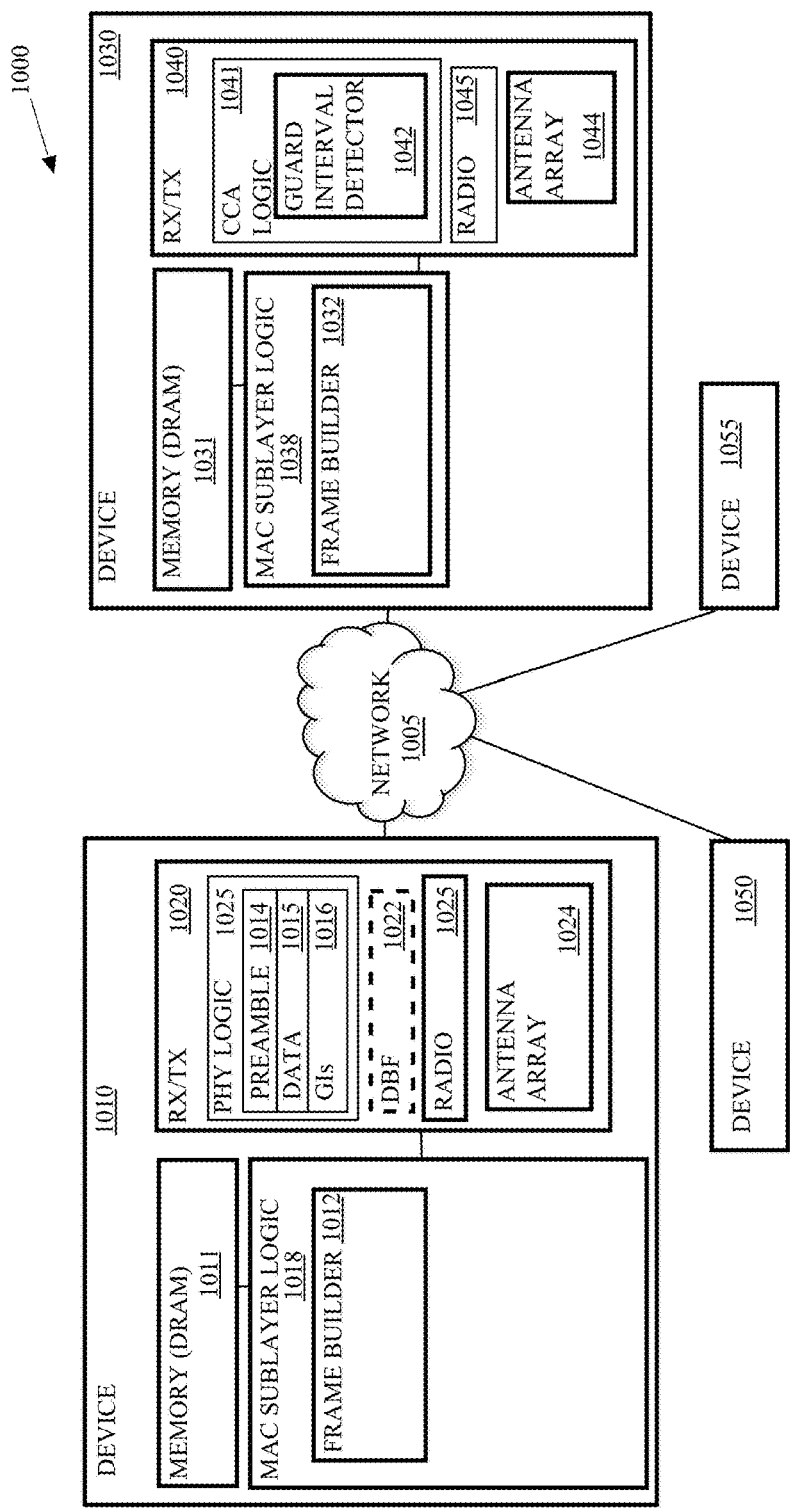
FIG. 1 depicts an embodiment of an example wireless network comprising a plurality of communications devices.

The following is a detailed description of novel embodiments depicted in the accompanying drawings. However, the amount of detail offered is not intended to limit anticipated variations of the described embodiments; on the contrary, the claims and detailed description are to cover all modifications, equivalents, and alternatives falling within the spirit and scope of the present teachings as defined by the appended claims. The detailed descriptions below are designed to make such embodiments understandable to a person having ordinary skill in the art.

Institute of Electrical and Electronic Engineers (IEEE) 802.11ah systems are in the standards development phase. The bandwidths currently defined are 1 MegaHertz (MHz) and a set of down-clocked IEEE 802.11ac bandwidths, namely 2, 4, 8 and 16 MHz. The 1 MHz bandwidth is not derived from the IEEE 802.11n/ac rates, and thus this bandwidth mode is being designed more or less independently. In IEEE 802.11n/ac systems when double bandwidth was defined, half of the bandwidth was defined as primary channel and the other half as secondary channel. For example, a 40 MHz channel consists of primary 20 MHz and secondary 20 MHz channels. To enable coexistence, standard specifications have defined Clear Channel Assessment (CCA) rules for both primary and secondary channels for the IEEE 802.11n/ac systems.

A clear channel assessment (CCA) function may be a logical function in the physical layer (PHY) that determines the current state of use of the wireless medium. CCA shall detect a medium busy condition when the carrier sense/clear channel assessment (CS/CCA) mechanism detects a channel busy condition. For the operating classes requiring CCA-Energy Detect (CCAED), CCA shall also detect a medium busy condition when CCA-ED detects a channel busy condition.

Similarly, devices such as IEEE 802.11ah devices will have defined CCA rules. IEEE 802.11ah devices are significantly different than IEEE 802.11ac devices in that the ratio of time spent transmitting data as compared to time spent transmitting a preamble is significantly smaller. In other words, the ratio of the preamble transmission time over the data transmission time for IEEE 802.11ac devices is much greater than for IEEE 802.11ah devices. As a result, the low power, IEEE 802.11ah devices are much more likely to wake from a power-save mode in the midst of a data portion of a packet transmission than during the preamble portion of the packet transmission. In such situations, CCA rules for IEEE 802.11ac devices may result in a higher probability of conflicts when the IEEE 802.11ah devices awake from a power-save mode into an active state or active mode.

In addition, with the adoption of a 1 MHz bandwidth occupying half of the 2 MHz bandwidth, possibly one-fourth of a 4 MHz bandwidth, one-eighth of an 8 MHz bandwidth, and one-sixteenth of a 16 MHz bandwidth, new coexistence situations arise with respect to IEEE 802.11ah devices. In IEEE 802.11n/ac, using the 40 MHz example, a 20 MHz bandwidth device could decode both halves of the 40 MHz signal field. This fact puts a new constraint in the design for CCA for IEEE 802.11ah devices and other devices in similar situations.

One of the target applications of IEEE 802.11ah devices is low power devices that are going to be in power save mode most of the time. For such devices, the chance to have a synchronized network allocation vector (NAV) timer is small. The NAV is an indicator, maintained by each station (STA), of time periods when transmission onto the wireless medium is not initiated by the STA regardless of whether the STA's clear channel assessment (CCA) function senses that the wireless medium is busy. Therefore, embodiments may implement CCA logic that takes into account the higher likelihood of awakening in the middle of a data transmission.

Embodiments may comprise logic for collision mitigation between transmissions of wireless transmitters and receivers operating at different bandwidths. In many embodiments, the receivers may be capable of receiving and detecting signals transmitted at wider and/or narrower bandwidths. In several embodiments, the receivers comprise CCA logic with a guard interval detector, or cyclic prefix detector, to detect transmissions on the primary channel. Many embodiments implement CCA logic that performs guard interval (GI) detection on the primary channel in addition to start of the packet detection and energy detection on the primary channel. In several embodiments, the CCA logic may also perform GI detection on a secondary channel or one or more non-primary channels. For instance, a 2 MHz receiver may implement a guard interval detector to detect 1 MHz bandwidth signals on the primary 1 MHz bandwidth channel and on the secondary 1 MHz bandwidth channel of the 2 MHz bandwidth channel with a primary frequency of, e.g., 900 MHz (MegaHertz)

In many embodiments, the process of the guard interval detector may be taken as part of CCA operation in CCA logic or coupled with CCA logic. In other embodiments, the guard interval detector can be implemented independently from the CCA operation. Once a device is ready to transmit a packet, the device may determine if the device is just exiting a power save mode and if its NAV timer is outdated or expired. If both are true, the device may also perform GI detection with logic such as the guard interval detector 1200 illustrated in FIG. 1D on a primary channel of the device's frequency bandwidth. Note that the normal start of the packet detection requires one OFDM symbol to detect the short training field (STF). However, according to data obtained through simulation studies, a reliable GI detection that can provide sensitivity level comparable to the start of the packet detection, implements N=4 symbols (see FIG. 1D). In such embodiments, the duration of N=4 symbols may be equivalent a short interframe space (SIFS) interval such that there may be no requirement for a new timing restriction for the CCA operation.

In some embodiments, the guard interval detector may comprise an antenna to receive the wide bandwidth signal. Such embodiments may comprise logic to select subcarriers of the primary channel from the wide bandwidth signal. In many embodiments, the signal on the primary channel is correlated against a delayed version of the signal the primary channel to compare peaks in the correlation to determine if one or more peaks are greater than a threshold correlation value. In response to this comparison, the guard interval detector may output an indication regarding whether or not a signal the primary channel is detected. In some embodiments, in response to detecting a guard interval on the primary channel, the receiving device may defer transmissions to avoid collision with the signal.

Some embodiments may provide, e.g., indoor and/or outdoor "smart" grid and sensor services. For example, some embodiments may provide sensors to meter the usage of electricity, water, gas, and/or other utilities for a home or homes within a particular area and wirelessly transmit the usage of these services to a meter substation. Further embodiments may utilize sensors for home healthcare, clinics, or hospitals for monitoring healthcare related events and vital signs for patients such as fall detection, pill bottle monitoring, weight monitoring, sleep apnea, blood sugar levels, heart rhythms, and the like. Embodiments designed for such services generally require much lower data rates and much lower (ultra low) power consumption than devices provided in IEEE 802.11n/ac systems.

Logic, modules, devices, and interfaces herein described may perform functions that may be implemented in hardware and/or code. Hardware and/or code may comprise software, firmware, microcode, processors, state machines, chipsets, or combinations thereof designed to accomplish the functionality.

Embodiments may facilitate wireless communications. Some embodiments may integrate low power wireless communications like Bluetooth®, wireless local area networks (WLANs), wireless metropolitan area networks (WMANs), wireless personal area networks (WPAN), cellular networks, Institute of Electrical and Electronic Engineers (IEEE) IEEE 802.11-2012, IEEE Standard for Information technology—Telecommunications and information exchange between systems—Local and metropolitan area networks—Specific requirements—Part 11: Wireless LAN Medium Access Control (MAC) and Physical Layer (PHY) Specifications (http://standards.ieee.org/getieee802/download/802.11-2012.pdf), communications in networks, messaging systems, and smart-devices to facilitate interaction between such devices. Furthermore, some wireless embodiments may incorporate a single antenna while other embodiments may employ multiple antennas.

Turning now to FIG. 1, there is shown an embodiment of a wireless communication system 1000. The wireless communication system 1000 comprises a communications device 1010 that is wire line or wirelessly connected to a network 1005. The communications device 1010 may communicate wirelessly with a plurality of communication devices 1050, and 1055 via the network 1005. The communications devices 1010, 1030, 1050, and 1055 may comprise sensors, stations, access points, hubs, switches, routers, computers, laptops, notebooks, cellular phones, PDAs (Personal Digital Assistants), or other wireless-capable devices.

The communications devices 1010, 1030, and 1055 may operate at a 2, 4, or 8 MHz bandwidth and the communications device 1050 may operate a 1 MHz bandwidth. With the adoption of a 1 MHz bandwidth occupying half of the 2 MHz bandwidth, a coexistence issue needs to be addressed when, e.g., a 2 MHz operation overlaps two 1 MHz channels, e.g., a primary channel and a secondary channel.

In some embodiments, coexistence issues may be reduced by rules for assigning primary and non-primary channels. In a 2 MHz basic service set (BSS), for instance, rules may state that a 1 MHz waveform may only be allowed at the lower side (lower 1 MHz band), which is referred to as a primary channel, and in a 4/8/16 MHz BSS, when primary 2 MHz is at lower most of the overall band, then 1 MHz may only be allowed at upper side of the 2 MHz primary channel. When primary 2 MHz is at upper most of the overall band, a 1 MHz may only be allowed at lower side of the 2 MHz primary channel. Based on this, a 2 MHz device, for example, can detect a 1 MHz transmission by performing clear channel assessment (CCA) on the specified lower (or upper) part of its bandwidth prior to start of its transmission; and hence avoid collision. Note that a 2 MHz device may be capable of receiving 1 MHz signal by selecting either of its primary or secondary sub-channels.

When a device such as communications device 1030 exits a power-save mode to enter an active mode, the CCA logic 1041 may make a measurement of the channel and most likely its CCA measurement will not coincide with another device's start of a packet transmission, but may be somewhere in the middle of transmission. In such a situation, the CCA logic 1041 may comprise a guard interval detector such as the guard interval detector 1042 to perform guard interval (GI) detection in parallel to the start of the packet (SOP) detection and energy detection (ED) on the primary channel such as the upper or lower 1 MHz bandwidth of a 2 MHz channel.

Figure 1D:
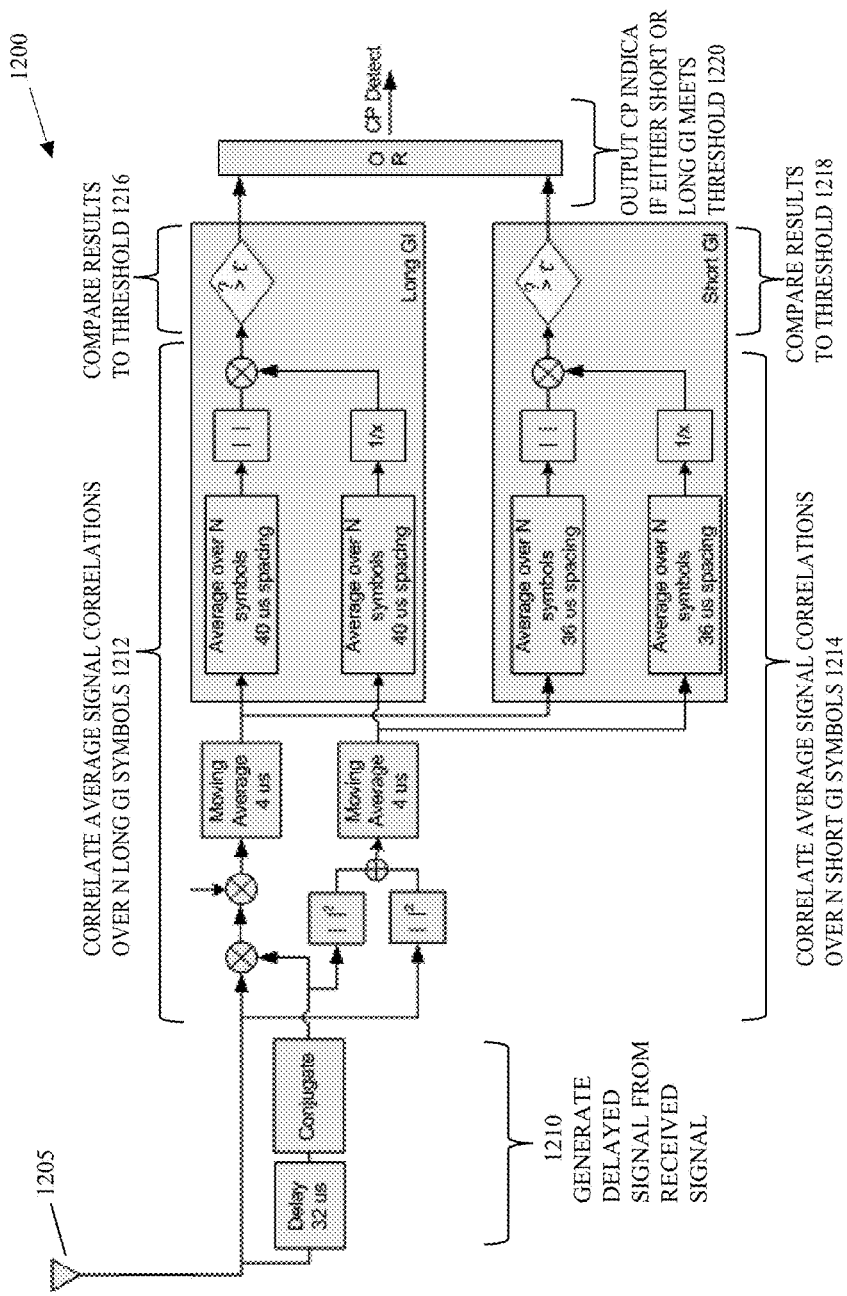
FIG. 1D depicts an embodiment of a guard interval detector for establishing communications between wireless communication devices.

As depicted in the guard interval (GI) detector 1200 of FIG. 1D, the received signal goes through the known Cyclic-Prefix (CP) (or GI) detection algorithm by searching for an identical 4 usec (microsecond) transmission after 32 usec of delay 1214. Note that the guard interval detectors 1042 and 1200 are described for operation of a 2 MHz device but may be implemented on devices of other bandwidths such as 4 MHz, 8 MHz, or 16 MHz. In some embodiments, the 2 MHz bandwidth devices implement additional 1 MHz bandwidth filtering to select a primary 1 MHz channel or a secondary 1 MHz channel. In other embodiments, devices such as communications devices 1010, 1030, and 1055 (2 MHz, 4 MHz, 8 MHz, and/or 16 MHz bandwidth operation) may not need filtering since these devices can select the sub-channels from a wider bandwidth channel. The guard interval detector 1042 and 1200 may be implemented on the primary channel in addition to the secondary channel.

Note also that IEEE 802.11ah OFDM symbol may be 32 usec long. In many embodiments, either ¼th or ⅛th of the OFDM time domain symbol is copied and inserted in front of the transmission as a CP that is named either a Long GI or a Short GI, respectively. The guard interval detector 1042 may detect such an identical transmission. In many embodiments, this detection may be done by correlating the signal by a delayed version of itself and searching for peaks of correlation that are greater than a known threshold value. In the case where the receiver is a 2 MHz device, the signal is first processed by the RF front-end and is bandlimited (using analog or digital filtering or sub-channel selection circuits) to the 1 MHz signal.

Once a device such as communications device 1030 is ready to transmit a packet, the communications device 1030 may determine if the communications device 1030 is exiting a power-save mode into an active mode and if its NAV timer is expired. If both are true, the communications device 1030 may perform GI detection with logic such as the guard interval detector 1042.

The guard interval detector 1042 of communications device 1030 may detect a guard interval (or cyclic prefix) of a transmission such as a 1 MHz bandwidth transmission by a receiver such as a 4 MHz bandwidth receiver to avoid a collision. The guard interval detector 1042 implements a detection method that makes use of the Guard Interval (GI) of an OFDM symbol. It is known that an OFDM symbol contains a repetition of a portion of its signal known as the GI. The GI detector 1042 exploits detection of, e.g., the GI of a 1 MHz signal in the 2 MHz signal bandwidth. Upon detection of such signal, the 2 MHz device recognizes ongoing 1 MHz transmission and would therefore defer its transmission. This way, collision of a 2 MHz transmission over the ongoing 1 MHz transmission is avoided.

For example, the communications device 1010 may comprise a metering substation for water consumption within a neighborhood of homes. Each of the homes within the neighborhood may comprise a communications device such as the communications device 1030 and the communications device 1030 may be integrated with or coupled to a water meter usage meter. Periodically, the communications device 1030 may awake from a power-save mode to initiate communications with the metering substation to transmit data related to water usage. The communications device 1030 may first check the channel to determine if the channel is clear prior to initiating a transmission. If the communications device 1030 just awoke from the power-save mode, the communications device 1030 may not have been in an active mode to receive the SOP of an on-going transmission. In other words, there is a possibility that the communications device 1030 awoke in the middle of a data transmission between other devices such as devices 1050 and 1055.

In response to determining that the communications device 1030 awake from a power-save mode, the communications device 1030 may check to see if the communications device 1030 comprises an updated network allocation vector (NAV). For instance, the communications device 1030, as a low power device, may have detected a NAV and determined to enter the power-save mode to wait until the NAV was about to expire for the purposes of conserving energy. Upon awakening, the communications device 1030 may retrieve the unexpired NAV to determine when an on-going transmission will end. If the NAV is unexpired, the CCA logic 1041 of the communications device 1030 may monitor the medium for a start of the packet and for energy indicative of a signal transmission to determine that the medium is clear before initiating a transmission.

On the other hand, if the NAV is expired, then the communications device 1030 may perform GI detection on the primary channel in addition to and in parallel with the start of the packet and energy detection to determine if the medium is not busy. Start of the packet detection may detect lowest signal level at shortest time duration due to detecting an STF. But if a device wakes up in the middle of packet, it would miss detecting the preamble (or the start of the packet) and hence it has a choice between energy detect or GI. Note that in many embodiments, the GI detection on the primary channel may be capable of detecting lower strength signals than the energy detection. For instance, the energy detection may detect energy of background noise and that noise my not be distinguishable from a signal by the energy detector so the threshold energy level to determine that a signal is being detected may be set at a relatively high energy level such as −75 dBm (decibels of measured power) for energy detection. The start of packet detection may detect signals with strengths such as −92 dBm or −98 dBm or higher and the GI detector 1042 may detect signals on the non-primary channels having strengths of, e.g., −92 dBm. In many embodiments, the GI detector 1042 may detect signals strengths on the primary channel that are weaker than the signal strengths that the energy detector can detect, reducing the probability of a collision between a signal transmitted by the communications device 1030 and another device that have an on-going transmission at the time that the communications device 1030 awakes from the power-save mode. Hence, some embodiments have the advantage of lowering the power consumption in the devices by implementing the CCA logic 1041 with the GI detector 1041 on the primary channel.

In further embodiments, the communications device 1010 may facilitate data offloading. For example, communications devices that are low power sensors may include a data offloading scheme to, e.g., communicate via Wi-Fi, another communications device, a cellular network, or the like for the purposes of reducing power consumption consumed in waiting for access to, e.g., a metering station and/or increasing availability of bandwidth. Communications devices that receive data from sensors such as metering stations may include a data offloading scheme to, e.g., communicate via Wi-Fi, another communications device, a cellular network, or the like for the purposes of reducing congestion of the network 1005.

The network 1005 may represent an interconnection of a number of networks. For instance, the network 1005 may couple with a wide area network such as the Internet or an intranet and may interconnect local devices wired or wirelessly interconnected via one or more hubs, routers, or switches. In the present embodiment, network 1005 communicatively couples communications devices 1010, 1030, 1050, and 1055.

The communication devices 1010 and 1030 comprise memory 1011 and 1031, and medium access control (MAC) sublayer logic 1018 and 1038, respectively. The memory 1011, 1031 such as dynamic random access memory (DRAM) may store the frames, preambles, and preamble structures 1014, or portions thereof. The frames, also referred to as MAC layer protocol data units (MPDUs), and the preamble structures 1014 may establish and maintain synchronized communications between the transmitting device and the receiving device. The preamble structures 1014 may also establish the communications format and rate. In particular, preambles generated or determined based upon the preamble structures 1014 may train, e.g., the antenna arrays 1024 and 1044 to communicate with each other, establish the modulation and coding scheme of the communications, the bandwidth or bandwidths of the communications, the length of the transmission vector (TXvector), the application of beamforming, and the like.

The MAC sublayer logic 1018, 1038 may generate the frames and the physical layer (PHY) logic 1025 may generate physical layer data units (PPDUs). More specifically, the frame builders 1012, 1032 may generate frames and the data unit builders of PHY logic such as PHY logic 1025 may generate PPDUs. The data unit builders may generate PPDUs by encapsulating payloads comprising the frames generated by frame builders as data 1015. Prior to transmission, the data unit builders may insert guard intervals (GIs) 1016 in the preamble and in the data 1015. GI insertion logic may insert the GIs 1016 in the PPDUs between OFDM symbols to attenuate, or potentially eliminate, inter-symbol interference (ISI), which might result from multi-path distortion. The GIs 1016 may also eliminate the need for a pulse-shaping filter and reduce the sensitivity of RX/TX 1020 to time synchronization problems. Assuming a GI of ⅛ of the symbol length is inserted between each symbol, the ISI can be avoided if the multipath time-spreading (the time between the reception of the first and the last echo) is shorter than the GI.

In many embodiments, a cyclic prefix (CP) is transmitted during the GIs 1016. The CP may consist of the end of an orthogonal frequency-division multiplexing (OFDM) symbol copied into the GI, and the GI is inserted and transmitted prior to the OFDM symbol. One reason that the guard interval may consists of a copy of the end of the OFDM symbol is so that the receiver will integrate over an integer number of sinusoid cycles for each of the multipaths when the receiver performs OFDM demodulation with the FFT.

In the present embodiment, the data unit builders may encapsulate the frames with preambles based upon preamble structures 1014 to prefix the payloads such as data 1015 to be transmitted over one or more RF channels. The function of a data unit builder is to assemble groups of bits into code words or symbols that make up the preambles as well as the payloads so the symbols can be converted into signals to transmit via antenna arrays 1024 and 1044, respectively.

Each data unit builder may supply a preamble structure 1014 comprising a signal field and store the preambles generated based upon the preamble structure 1014 in the memory 1011, 1031 while the preambles are being generated and/or after the preambles are generated. In the present embodiment, the preamble structure 1014 may comprise one short training field (STF) and one long training field (LTF) prior to the signal field and the data 1015. The STF and the LTF may train the antenna arrays 1022 and 1042 to communicate with each other by making measurements related to communications such as measurements related to relative frequency, amplitude, and phase variations between quadrature signals. In particular, the STF may be used for packet detection, automatic gain control, and coarse frequency estimation. The LTF may be used for channel estimation, timing, and fine frequency estimation for a spatial channel.

The signal field provides data related to establishing communications including, for example, bits representing the modulation and coding scheme MCS, bandwidth, length, beamforming, space time block coding (STBC), coding, aggregation, short guard interval (Short GI), cyclic redundancy check (CRC), and a tail. In some embodiments, for instance, the signal field may comprise an MCS including Binary Phase-Shift Keying (BPSK) with a coding rate of ½ or a 256-point constellation, Quadrature Amplitude Modulation (256-QAM) with a coding rate of %. In further embodiments, the signal field includes a modulation technique such as Staggered-Quadrature, Phase-Shift Keying (SQPSK). In many embodiments, the MCS establishes communication with 1 to 4 spatial streams.

The communications devices 1010, 1030, 1050, and 1055 may each comprise a transceiver (RX/TX) such as transceivers (RX/TX) 1020 and 1040. Each transceiver 1020, 1040 comprises a radio comprising an RF transmitter and an RF receiver. Each RF transmitter impresses digital data onto an RF frequency for transmission of the data by electromagnetic radiation. An RF receiver receives electromagnetic energy at an RF frequency and extracts the digital data therefrom. FIG. 1 may depict a number of different embodiments including a Multiple-Input, Multiple-Output (MIMO) system with, e.g., four spatial streams, and may depict degenerate systems in which one or more of the communications devices 1010, 1030, 1050, and 1055 comprise a receiver and/or a transmitter with a single antenna including a Single-Input, Single Output (SISO) system, a Single-Input, Multiple Output (SIMO) system, and a Multiple-Input, Single Output (MISO) system. The wireless communication system 1000 of FIG. 1 is intended to represent an Institute for Electrical and Electronics Engineers (IEEE) 802.11ah system. Similarly, devices 1010, 1030, 1050, and 1055 are intended to represent IEEE 802.11ah devices although embodiments claimed herein may comprise other types of devices.

In many embodiments, transceivers 1020 and 1040 implement orthogonal frequency-division multiplexing (OFDM). OFDM is a method of encoding digital data on multiple carrier frequencies. OFDM is a frequency-division multiplexing scheme used as a digital multi-carrier modulation method. A large number of closely spaced orthogonal sub-carrier signals are used to carry data. The data is divided into several parallel data streams or channels, one for each sub-carrier. Each sub-carrier is modulated with a modulation scheme at a low symbol rate, maintaining total data rates similar to conventional single-carrier modulation schemes in the same bandwidth.

An OFDM system uses several carriers, or "tones," for functions including data, pilot, guard, and nulling. Data tones are used to transfer information between the transmitter and receiver via one of the channels. Pilot tones are used to maintain the channels, and may provide information about time/frequency and channel tracking And guard tones may help the signal conform to a spectral mask. The nulling of the direct component (DC) may be used to simplify direct conversion receiver designs. And guard intervals may be inserted between symbols such as between every OFDM symbol as well as between the short training field (STF) and long training field (LTF) symbols of the preamble in the front end of the transmitter during transmission to avoid inter-symbol interference (ISI), which might result from multi-path distortion.

In one embodiment, the communications device 1010 optionally comprises a digital beam former (DBF) 1022, as indicated by the dashed lines. The DBF 1022 transforms information signals into signals to be applied to elements of an antenna array 1024. The antenna array 1024 is an array of individual, separately excitable antenna elements. The signals applied to the elements of the antenna array 1024 cause the antenna array 1024 to radiate one to four spatial channels. Each spatial channel so formed may carry information to one or more of the communications devices 1030, 1050, and 1055. Similarly, the communications device 1030 comprises a transceiver 1040 to receive and transmit signals from and to the communications device 1010. The transceiver 1040 may comprise an antenna array 1044 and, optionally, a DBF 1042. In parallel with digital beam forming, the transceiver 1040 is capable of communicating with IEEE 802.11ah devices.

FIG. 1A depicts an embodiment of a physical layer protocol data unit (PPDU) 1060 with a preamble structure 1062 for establishing communications between wireless communication devices such as communications devices 1010, 1030, 1050, and 1055 in FIG. 1. The PPDU 1060 may comprise a preamble structure 1062 including orthogonal frequency division multiplexing (OFDM) training symbols for a single multiple input, multiple output (MIMO) stream followed by a signal field, followed by additional OFDM training symbols for additional MIMO streams, and the preamble structure 1060 may be followed by the data payload. In particular, the PPDU 1060 may comprise a short training field (STF) 1064, a long training field (LTF) 1066, the 11AH-SIG 1068, additional LTFs 1069, and data 1070. The STF 1064 may comprise a number of short training symbols.

The LTF 1066 may comprise a GI and two long training symbols. The 11ah-SIG 1068 may comprise a GI and signal field symbols such as the symbols described in FIG. 1C. The additional LTFs 1069 may comprise one or more LTF symbols for additional MIMO streams. The data 1070 may comprise one or more MAC sublayer protocol data units (MPDUs) and may include one or more GIs between OFDM symbols.

FIG. 1B depicts an alternative embodiment of a physical layer protocol data unit (PPDU) 1080 with a preamble structure 1082 for establishing communications between wireless communication devices such as communications devices 1010, 1030, 1050, and 1055 in FIG. 1. The PPDU 1080 may comprise a preamble structure 1082 including orthogonal frequency division multiplexing (OFDM) training symbols for a single multiple input, multiple output (MIMO) stream followed by a signal field, and the data payload may follow the preamble structure 1080. In particular, the PPDU 1080 may comprise a short training field (STF) 1064, a long training field (LTF) 1066, the 11AH-SIG 1068, and data 1070.

FIG. 1C depicts an embodiment of a signal field, 11AH-SIG 1100 for establishing communications between wireless communication devices such as communications devices 1010, 1030, 1050, and 1055 in FIG. 1. While the number, types, and content of the fields may differ between embodiments, the present embodiment may comprise a signal field with a sequence of bits for a modulation and coding scheme (MCS) 1104 parameter, a bandwidth (BW) 1106 parameter, a length 1108 parameter, a beamforming (BF) 1110 parameter, a space-time block coding (STBC) 1112 parameter, a coding 1114 parameter, an aggregation 1116 parameter, a short guard interval (SGI) 1118 parameter, a cyclic redundancy check (CRC) 1120 parameter, and a tail 1122 parameter.

The MCS 1104 parameter may designate a modulation and coding scheme such as binary phase-shift keying (BPSK), 16-point constellation quadrature amplitude modulation (16-QAM), 64-point constellation quadrature amplitude modulation (64-QAM), 256-point constellation quadrature amplitude modulation (256-QAM), quadrature phase-shift keying (QPSK), or staggered quadrature phase-shift keying (SQPSK) as a modulation format for a communication. The selections may offer one to four spatial streams for the communication. The BPSK may have a coding rate of ½. The 256-QAM may have a coding rate of ¾. And the SQPSK, also referred to as OQPSK, may have a coding rate of ½ or ¾. In some embodiments, SQPSK is an allowed modulation format on the signal and data fields to extend the range of operation of the communications devices for, e.g., outdoor sensor monitoring.

The BW 1106 parameter may involve selecting a bandwidth from bandwidths such as 2 MHz, 4 MHz, 8 MHz, and 16 MHz. Selection of a fifth bandwidth such as 1 MHz may also be selected via another method. In other embodiments, the BW 1106 parameter may offer four different bandwidths.

The length 1108 parameter may describe the length of the transmit vector in octets. In some embodiments, the allowed values for the length 1108 parameter are in the range of 1 to 4095. The length 1108 parameter may indicate the number of octets in the MAC protocol data unit (MPDU) that the MAC sublayer logic is currently requesting the physical layer (PHY) device, e.g., the transceiver RX/TX 1020, 1040 in FIG. 1, to transmit. The length 1108 parameter is used by the PHY to determine the number of octet transfers that will occur between the MAC and the PHY after receiving a request to start the transmission.

The beamforming (BF) 1110 parameter may designate whether or not the PHY will implement beamforming for transmission of the MPDU. The space-time block coding (STBC) 1112 parameter may designate whether or not to implement a space-time block coding such as Alamouti's code. And the coding 1114 parameter may designate whether to use binary convolutional coding (BCC) or low density parity check coding (LDPC).

The aggregation 1116 parameter may designate whether or not to mandate MPDU aggregation (A-MPDU). The short guard interval (SGI) 1118 parameter may designate the duration of the SGI. For example, one bit may be set to a logical one to designate a short guard interval or set to a logical zero to designate a long guard interval and a second bit may designate short guard interval length ambiguity mitigation.

The cyclic redundancy check (CRC) 1120 sequence parameter may comprise a hash of 11ah-SIG 1100 for error checking and the tail 1122 parameter may comprise a bit sequence of, e.g., logical zeros or ones, to designate the end of the signal field, 11ah-SIG 1100.

FIG. 1D illustrates an embodiment 1200 of a guard interval detector coupled with an antenna 1205. First, a signal such as a 1 MHz signal is received by the RF front-end of the wideband device such as a 2 MHz device. Note that 2, 4, 8, and 16 MHz bandwidth devices may include guard interval detectors that do not comprise the 1 MHz filtering in the receiver front-end because these devices can decode the narrower bandwidth signals and select sub-channels or sub-carriers. Then, this signal goes through the known Cyclic-Prefix (CP) (or GI) detection algorithm by searching for an identical 4 usec transmission after 32 usec of delay 1210. Note that IEEE 802.11ah OFDM symbol may be 32 usec long, either ¼th or ⅛th of the signal is copied and inserted in front of the transmission as CP that is named either Long GI or Short GI. The present embodiment may detect an identical transmission. This detection may be performed by correlating the signal with a delayed version of itself and searching for peaks of correlation that are greater than a known threshold value 1216 and 1218 for an average of "N" CP symbols for the long GI 1212 and the short GI 1214.

If the peaks of correlation of the received signal and the delayed signal averaged over N symbols of the short GI or the long GI are greater than the threshold(s) 1216 and 1218, the output of the GI detector outputs an indication that the GI detector detected CPs. In response to a positive indication of detection of CPs, the communications device 1030 may determine not to transmit but, instead to wait for the transmission to complete or to enter a power-save mode for a period of time, deferring a transmission of data to a data collection station such as communications device 1055.

On the other hand, if the peaks of correlation of the received signal and the delayed signal averaged over N symbols of the short GI or the long GI are less than the threshold(s) 1216 and 1218, the output of the GI detector may output an indication that the GI detector did not detect CPs or generates no output. In response to a negative indication or lack of an indication of detection of CPs, the communications device 1030 may determine based upon the start of the packet detection and/or energy detection whether or not to transmit data to a data collection station such as communications device 1055.

Figure 2:
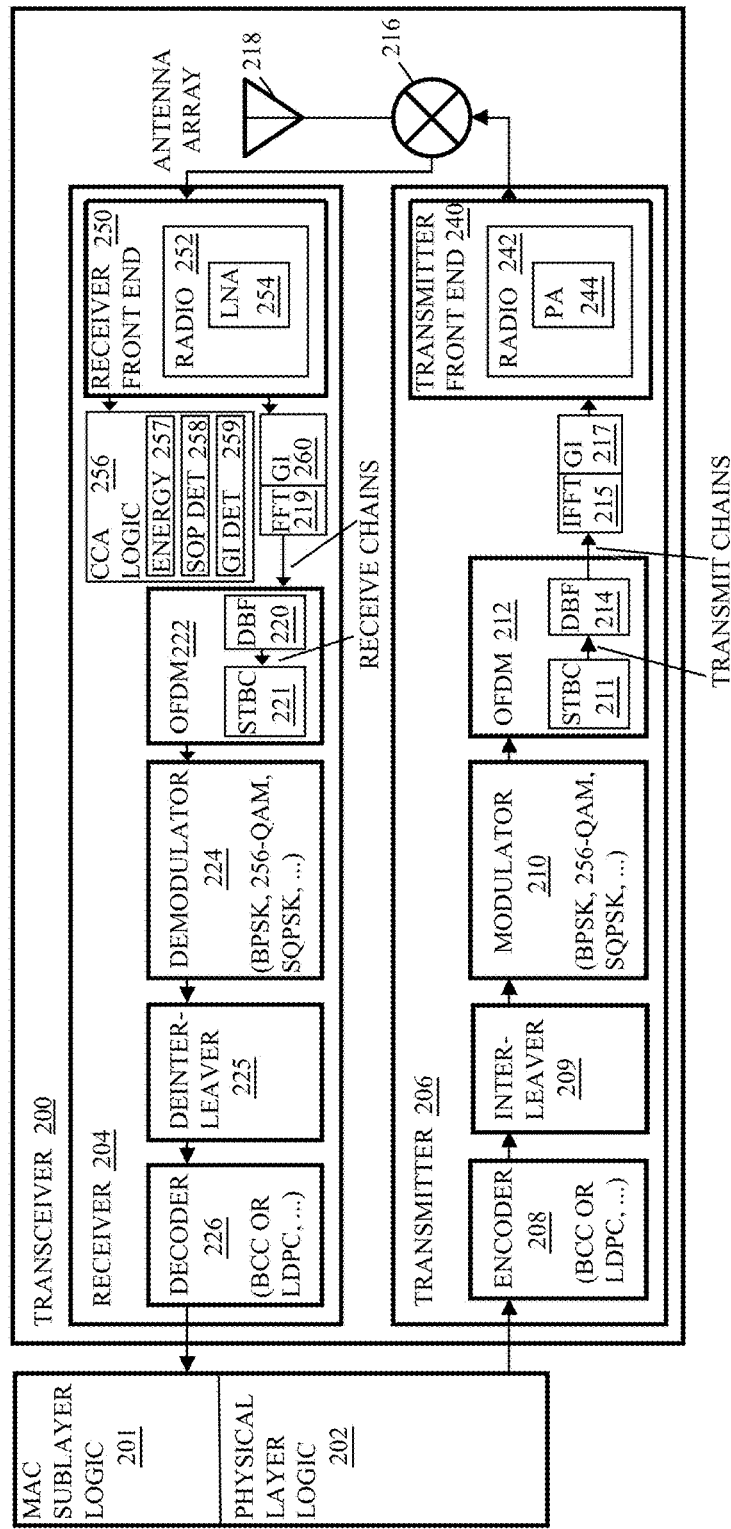
FIG. 2 depicts an embodiment of an apparatus for guard interval detection for collision mitigation between transmissions of wireless transmitters and receivers operating at different bandwidths.

FIG. 2 illustrates an embodiment of an apparatus to transmit an orthogonal frequency division multiplexing (OFDM)-based communication in a wireless network. The apparatus comprises a transceiver 200 coupled with medium access control (MAC) sublayer logic 201 and a physical layer (PHY) logic 250. The MAC sublayer logic 201 and PHY layer logic 250 may generate a physical layer protocol data unit (PPDU) to transmit via transceiver 200.

The MAC sublayer logic 201 may comprise hardware and/or code to implement data link layer functionality including generation of MAC protocol data units (MPDUs) from MAC service data units (MSDUs) by encapsulating the MSDUs in frames via a frame builder. For example, a frame builder may generate a frame including a type field that specifies whether the frame is a management, control or data frame and a subtype field to specify the function of the frame. A control frame may include a Ready-To-Send or Clear-To-Send frame. A management frame may comprise a Beacon, Probe Response, Association Response, and Reassociation Response frame type. The duration field that follows the first frame control field specifies the duration of this transmission. A duration field may include the Network Allocation Vector (NAV), which can be used as a protection mechanism for communications. And the data type frame is designed to transmit data. An address field may follow the duration field, specifying the address of the intended receiver or receivers for the transmission.

The PHY logic 202 may comprise a data unit builder. The data unit builder may determine a preamble based upon a preamble structure such as the preamble structure illustrated in FIG. 1C to encapsulate the MPDU to generate a PPDU. In many embodiments, the data unit builder may select a preamble from memory such as a default preamble for data frame transmissions, control frame transmissions, or management transmissions. In several embodiments, the data unit builder may create the preamble based upon a default set of values for the preamble received from another communications device. For example, a data collection station compliant with IEEE 802.11ah for a farm may periodically receive data from low power sensors that have integrated wireless communications devices compliant with IEEE 802.11ah. The sensors may enter a low power mode for a period of time, wake to collect data periodically, and communicate with the data collection station periodically to transmit the data collected by the sensor. In some embodiments, the sensor may proactively initiate communications with the data collection station, transmit data indicative of a communications capability, and begin communicating the data to the data collection station in response to a CTS or the like. In other embodiments, the sensor may transmit data to the data collection station in response to initiation of communications by the data collection station.

The data unit builder may generate the preamble including an STF, an LTF, and an 11ah-SIG field with one or more GIs. In many embodiments, the data unit builder may create the preamble based upon communications parameters chosen through interaction with another communications device.

The transceiver 200 comprises a receiver 204 and a transmitter 206. The transmitter 206 may comprise one or more of an encoder 208, a modulator 210, an OFDM 212, and a DBF 214. The encoder 208 of transmitter 206 receives data destined for transmission from the MAC sublayer logic 202. The MAC sublayer logic 202 may present data to transceiver 200 in blocks or symbols such as bytes of data. The encoder 208 may encode the data using any one of a number of algorithms now known or to be developed. Encoding may be done to achieve one or more of a plurality of different purposes.

In the present embodiment, the encoder 208 may implement a binary convolutional coding (BCC) or a low density parity check coding (LDPC), as well as other encodings.

The modulator 210 of transmitter 206 receives data from encoder 208. A purpose of modulator 210 is to transform each block of binary data received from encoder 208 into a unique waveform that can be transmitted by an antenna upon up-conversion and amplification. The modulator 210 impresses the received data blocks onto a sinusoid of a selected frequency. More specifically, the modulator 210 maps the data blocks into a corresponding set of discrete amplitudes of the sinusoid, or a set of discrete phases of the sinusoid, or a set of discrete frequency shifts relative to the frequency of the sinusoid. The output of modulator 210 is a band pass signal.

In one embodiment, the modulator 210 may implement Quadrature Amplitude Modulation (QAM) impressing two separate k-bit symbols from the information sequence onto two quadrature carriers, $\cos(2\pi ft)$ and $\sin(2\pi ft)$. QAM conveys two digital bit streams, by changing (modulating) the amplitudes of two carrier waves, using the amplitude-shift keying (ASK) digital modulation scheme. The two carrier waves are out of phase with each other by 90° and are thus called quadrature carriers or quadrature components. The modulated waves are summed, and the resulting waveform is a combination of both phase-shift keying (PSK) and amplitude-shift keying (ASK). A finite number of at least two phases and at least two amplitudes may be used.

The output of modulator 210 may be fed to an orthogonal frequency division multiplexer (OFDM) 212 via a space-time block coding (STBC). OFDM 212 impresses the modulated data from modulator 210 onto a plurality of orthogonal sub-carriers. The output of the OFDM 212 is fed to the digital beam former (DBF) 214. Digital beam forming techniques are employed to increase the efficiency and capacity of a wireless system. Generally, digital beam forming uses digital signal processing algorithms that operate on the signals received by, and transmitted from, an array of antenna elements to achieve enhanced system performance. For example, a plurality of spatial channels may be formed and each spatial channel may be steered independently to maximize the signal power transmitted to and received from each of a plurality of user terminals. Further, digital beam forming may be applied to minimize multi-path fading and to reject co-channel interference.

The transmitter 206 may comprise an inverse fast Fourier transform logic 215 to transform the OFDM symbols to the time domain and a GI insertion logic 217 to insert GIs between OFDM symbols in the transmit chains. In many embodiments, the GIs may be short GIs or long GI and may comprise a copy of a number bits from the end of the OFDM symbols.

After the GIs are inserted into the signal, the transmitter front end 240 may prepare the signal for transmission. In many embodiments, a radio 242 of the transmitter front end 240 may comprise a power amplifier (PA) 244 to amplify the signal prior to transmitting the signal via an antenna array 218. In several embodiments, lower power devices may not include the power amplifier 244 or may include a capability to bypass the power amplifier 244 in order to reduce power consumption. The transceiver 200 may also comprise duplexers 216 connected to the antenna array 218. Thus, in this embodiment, a single antenna array is used for both transmission and reception. When transmitting, the signal passes through duplexers 216 and drives the antenna with the up-converted information-bearing signal. During transmission, the duplexers 216 prevent the signal to be transmitted from entering receiver 204. When receiving, information bearing signal received by the antenna array pass through duplexers 216 to deliver the signal from the antenna array to receiver 204. The duplexers 216 then prevent the received signals from entering transmitter 206. Thus, duplexers 216 operate as switches to alternately connect the antenna array elements to the receiver 204 and the transmitter 206.

Antenna array 218 radiates the information bearing signals into a time-varying, spatial distribution of electromagnetic energy that can be received by an antenna of a receiver. The receiver can then extract the information of the received signal. An array of antenna elements can produce multiple spatial channels that can be steered to optimize system performance. Reciprocally, multiple spatial channels in the radiation pattern at a receive antenna can be separated into different spatial channels. Thus, a radiation pattern of antenna array 218 may be highly selective. The antenna array 218 may be implemented using printed circuit board metallization technology. Microstrips, striplines, slotlines, and patches, for example, are all candidates for the antenna array 218.

The transceiver 200 may comprise a receiver 204 for receiving, demodulating, and decoding information bearing signals. The receiver 204 may comprise a receiver front end 250 with a radio 252 with a low noise amplifier 254 to remove the carrier at the primary frequency and amplify the signal. The receiver may also comprise clear channel assessment (CCA) logic 256 to determine whether a signal is being transmitted on a wireless medium for the purposes of determining whether the transmitter 206 can transmit a communication on the wireless medium.

The CCA logic 256 may comprise one or more different signal detectors to determine if the medium is busy. In the present embodiment, the CCA logic 256 comprises an energy detector 257, a start of the packet (SOP) detector 258, and a GI detector 259. The energy detector 257 may compare the energy of received by the antenna against a threshold energy level, in several embodiments, to distinguish noise energy from signal energy. The SOP detector 258 may monitor the incoming signals for an indication of the beginning of a packet being transmitted over the wireless medium. And the GI detector 259 may detect GIs in signals on the primary channel and, in some embodiments, on one or more non-primary channels of the transceiver's 200 bandwidth. For example, if the transceiver 200 is capable of transmitting at a 16 MHz bandwidth on a primary frequency of, e.g., 900 MHz the transceiver 200 may perform GI detection for one or more 1 MHz bandwidth signals, 2 MHz bandwidth signals, 4 MHz bandwidth signals, and 8 MHz bandwidth signals on the primary frequency of 900 MHz. In several embodiments, the GI detector 259 may comprise detection logic such as the GI detection logic 1200 illustrated in FIG. 1D.

The receiver 204 may comprise GI removal logic 260 to remove the GIs from the received signal and a fast Fourier transform (FFT) 219 to transform the time domain signal into a frequency based signal. The receiver 204 may also comprise one or more of a DBF 220, an OFDM 222, a demodulator 224 and a decoder 226. The received signals are fed from antenna elements 218 to a DBF 220. The DBF 220 transforms N antenna signals into L information signals.

The output of the DBF 220 is fed to the OFDM 222. The OFDM 222 extracts signal information from the plurality of subcarriers onto which information-bearing signals are modulated.

The demodulator 224 demodulates the received signal. Demodulation is the process of extracting information from the received signal to produce an un-demodulated information signal. The method of demodulation depends on the method by which the information is modulated onto the received carrier signal. Thus, for example, if the modulation is BPSK, demodulation involves phase detection to convert phase information to a binary sequence. Demodulation provides to the decoder a sequence of bits of information. The decoder 226 decodes the received data from the demodulator 224 and transmits the decoded information, the MPDU, to the MAC sublayer logic 202.

Persons of skill in the art will recognize that a transceiver may comprise numerous additional functions not shown in FIG. 2 and that the receiver 204 and transmitter 206 can be distinct devices rather than being packaged as one transceiver. For instance, embodiments of a transceiver may comprise a dynamic random access memory (DRAM), a reference oscillator, filtering circuitry, synchronization circuitry, possibly multiple frequency conversion stages and multiple amplification stages, etc. Further, some of the functions shown in FIG. 2 may be integrated. For example, digital beam forming may be integrated with orthogonal frequency division multiplexing.

Figure 3:
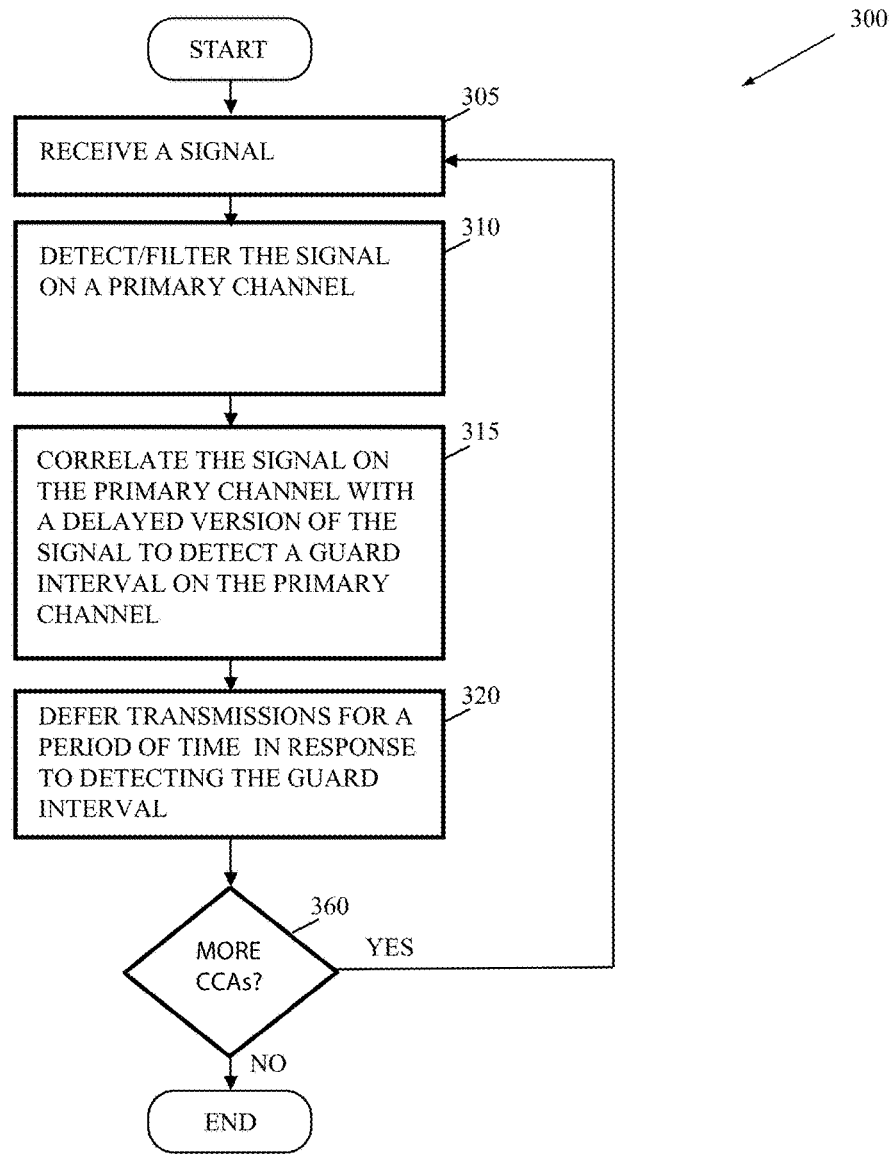
FIG. 3 depicts an embodiment of a flowchart for collision mitigation between transmissions of wireless transmitters and receivers operating at different bandwidths.

FIG. 3 depicts a flowchart 300 for mitigating collisions between transmissions such as the embodiments illustrated in FIGS. 1 and 1A-D. The flowchart 300 begins with receiving a signal at element 305. A communications device may awake from a power-save mode and determine to transmit data to a data collection station. Prior to transmitting the data to the data collection station, the communications device may perform a clear channel assessment (CCA) to determine if the data can be transmitted without colliding with an ongoing transmission.

To perform the CCA, CCA logic coupled with the receiver of the communications device may employ one or more detectors to determine if a signal is currently being transmitted on a channel of a wireless medium. In many embodiments, the CCA logic may perform carrier sense and energy detection on a primary channel of the communications device. The primary channel may be, for instance, the upper half or the lower half of the bandwidth of the communications device. In such embodiments, the other half of the bandwidth may be designated as a secondary channel. In some embodiments, part a certain bandwidth of the channel may be designated as a primary channel and other portions of the bandwidth may be designated as non-primary channels. To illustrate, if the communications device is a 4 MHz bandwidth device on a 900 MHz primary frequency, the primary channel may comprise the lower 2 MHz bandwidth of the 4 MHz channel and the secondary channel may comprise the upper 2 MHz bandwidth of the 4 MHz channel. In further embodiments, the primary channel may comprise a 1 MHz bandwidth channel and the non-primary channel may comprise the other three 1 MHz bandwidth channels. In still other embodiments, the primary channel and the non-primary channels may comprise one or more different bandwidth channels on the same primary frequency. In some embodiments, the primary and non-primary channels are defined in a specification for compatible devices. In other embodiments, the primary and non-primary channels may be defined by a coordinator such as an access point for a group or network of devices. In further embodiments, specifications may guide the designations depending upon the numbers and/or types of devices operating in a network or group of devices.

After receiving the signal, the CCA logic of the communications device may detect or filter the signal to obtain the signal on the primary channel (element 310). In many embodiments, the wide bandwidth device may be capable of capturing the primary channel without a need to filter the signal or the device may filter the signal by selecting only the sub-carriers associated with the primary channel. In other embodiments, the communications device may implement a bandwidth filter to select the primary channel.

Upon determining the signal on the primary channel, the CCA logic of the communications device may correlate the signal on the primary channel with a delayed version of the signal to detect a guard interval (GI) on the primary channel (element 315). In response to detecting the GI on the primary channel, the CCA logic may determine that a signal is being transmitted on the primary channel and may defer transmission for a period of time (element 320). In some embodiments, for instance, the determination that the GI on the primary channel may be sufficient to cause the CCA to determine an indication of the medium being busy. In further embodiments, the CCA logic may determine that the existence of the GI on the primary channel is associated with a probability, the energy detection is associated with a probability, and the start of the packet detection is associated with a probability. The CCA logic may determine, based upon the probabilities associated with each of the signal detectors, a probability that a signal exists on the primary channel and may determine whether or not to indicate the wireless medium is busy based upon the results and probabilities associated with each or a combination of the signal detectors. In many embodiments, the CCA logic may also determine whether a GI is detected on one or more non-primary channels and take such determinations into consideration in determining whether or not the medium is busy.

In many embodiments, the communications device may base a decision on whether the medium is busy or not on the output of the CCA logic over a period of time. For instance, the communications device may monitor the output for consistency that the medium is busy or the medium is not busy over a time period of microseconds, over a time period of milliseconds, a period of cycles of the carrier, or the like. In response to determining that the medium is busy, the CCA logic may follow rules associated with a determination that the medium is busy. For instance, in some embodiments, the rules may indicate that the communications device should defer the data transmission, re-enter a power-save mode, and awake at a later time to perform a new CCA to determine whether or not to transmit data to a data collection station (element 360). Further embodiments may comprise rules that indicate that the device should wait in a power-save mode until the next scheduled time period for transmission of data to a data collection device. Other embodiments may comprise rules that indicate that the device should wait for the end of the transmission and then perform a new CCA (element 360).

Figure 4:
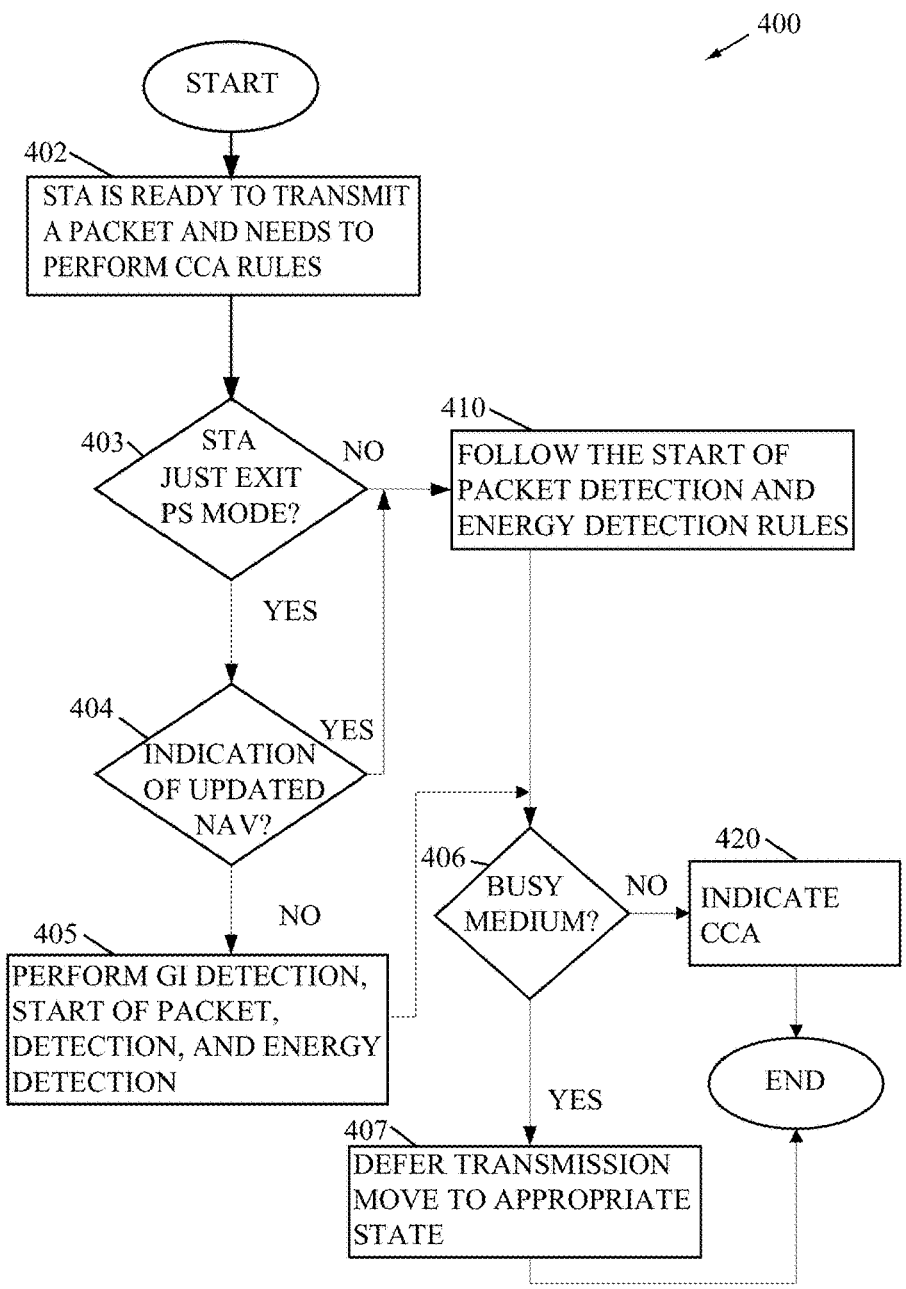
FIG. 4 depicts an embodiment of a flowchart for collision mitigation between transmissions of wireless transmitters and receivers operating at different bandwidths.

The flowchart 400 given in FIG. 4 describes an embodiment of a process performed by the CCA logic such as CCA logic 1041 or CCA logic described in conjunction with one or more of the embodiments illustrated in FIGS. 1-3. The flowchart 400 begins with a station (STA) that is ready to transmit a packet to a second STA and needs to perform CCA rules (element 402). For instance, the STA may be ready to transmit sensor data collected over a period of time since the last scheduled packet transmission.

Once the STA is ready to transmit a packet, CCA logic of the STA may determine whether or not the STA just exited a power-save mode and entered an active mode (element 403). If the STA did not just awake from a power-save mode to enter an active mode, the STA may have detected a start of the packet and/or received an updated NAV to determine the next time the medium may be available for transmission or that the medium is available for a packet transmission. If the STA did not just awake, the STA may follow a standard CCA rules by implementing start of the packet detection and energy detection (element 410). In some embodiments, the CCA rules may also include a GI detection on a non-primary frequency.

If, on the other hand, the STA just exited the power-save mode to enter an active mode, there is a possibility that the STA awoke in the middle of a packet transmission by another STA. In some embodiments, the STA may have received an updated NAV and interpreted the NAV to determine that the STA should enter a power-save mode until the NAV is closer to expiration. Thus, in several embodiments, the STA may determine if the NAV is updated or unexpired. If the NAV is unexpired, the STA may await the expiration of the NAV and/or follow the standard CCA rules by implementing start of the packet detection and energy detection (element 410).

If the STA determines that the STA just awoke from a power-save mode and the NAV timer is expired, the STA may perform GI detect on the primary channel with logic such as the GI detector 1200 illustrated in FIG. 1D in parallel with the start of the packet detection and the energy detection on the primary channel (element 405). For 2, 4, 8, and 16 MHz bandwidth devices, unlike 1 MHz device, the higher bandwidth transmission may duplicate the preamble and SIGNAL field. For example, a 2 MHz bandwidth device can decode the 4 MHz bandwidth SIGNAL field and can have accurate NAV information, but this happens only if the 2 MHz bandwidth device is awake and able to receive a start of the packet and decode the SIGNAL field. The advantage of some embodiments that implement such a procedure for higher bandwidth devices is that they can stay in power save mode more often.

To check the channel, the GI detector may receive a 1 MHz bandwidth transmission, bandlimit the signal to a 1 MHz, primary channel signal, and transmit the signal down parallel paths to a GI detection logic or detector, wherein at least one of the parallel paths is delayed. The GI detector may correlate the primary channel signal with the delayed version of the primary channel signal and compare peaks of correlation with a threshold value. If the peaks exceed a threshold value, the GI detector may determine that a 1 MHz bandwidth transmission is on the primary channel and, in response thereto, defer transmission for a period of time to allow the transmission to complete before attempting to transmit.

After performing the start of the packet detection and energy detection (element 410) or GI detect on the primary channel in parallel with the start of the packet detection and the energy detection on the primary channel (element 405), the CCA logic may determine whether or not to indicate clear channel assessment as the medium is not busy. In some embodiments, for instance, the CC logic may determine if any of the signal detection methods indicate that the medium is busy (element 406). If none of the detection methods resulted in an affirmative decision that the medium is busy, the CCA logic may indicate a CCA that the medium is not busy to the MAC sublayer logic (element 420).

After performing the start of the packet detection and energy detection (element 410) or GI detect on the primary channel in parallel with the start of the packet detection and the energy detection on the primary channel (element 405), the CCA logic may determine that the clear channel assessment indicates that the medium is busy so the communications device may defer transmission and transition into an appropriate state (element 407). In some embodiments, for instance, the CCA logic may determine that if not all of the signal detection methods indicate that the medium is not busy (element 406) that the transmission should be deferred.

The following examples pertain to further embodiments. One example comprises a method. The method may involve performing guard interval detection on a primary channel on the primary frequency in addition to start of the packet detection and energy detection on the primary channel and guard interval detection on a non-primary channel on the primary frequency to determine if a medium is busy in response to entering an active mode from a power-save mode; determining whether the medium is busy based upon the performing; and outputting an indication that the medium is busy to defer transmissions for a period of time in response to determining that the medium is busy.

In some embodiments, the method may further comprise outputting a clear channel assessment indicating that the medium is not busy in response to determining that the medium is not busy. In some embodiments, the method may further comprise determining whether a station has transitioned from the power save mode to the active mode; determining whether a network allocation vector is unexpired; and following start of packet detection and energy detection and guard interval detection on a non-primary channel of the primary frequency rules if the station did not enter the active mode from the power-saving mode or if there is an indication that the network allocation vector is updated. In many embodiments, the method may further comprise determining that a network allocation vector is not updated. In several embodiments, performing the guard interval detection on the primary channel of the primary frequency comprises: receiving, by a device, a signal on the primary frequency; selecting the signal on the primary channel; and correlating the signal on the primary channel to detect a guard interval in the signal on the primary channel. In some embodiments, correlating comprises comparing peaks in the correlation to determine if one or more peaks are greater than a threshold correlation value. And, in some embodiments, correlating comprises correlating the signal on the primary channel against a delayed version of the signal on the primary channel.

At least one computer program product to mitigate collisions between transmissions of devices operating at different bandwidths on a primary frequency of operation, the computer program product comprising a computer useable medium having a computer useable program code embodied therewith, the computer useable program code comprising computer useable program code configured to perform operations, the operations to carry out a method according to any one or more or all of embodiments of the method described above.

At least one system comprising hardware and code may carry out a method according to any one or more or all of embodiments of the method described above.

Another example comprises an apparatus. The apparatus may comprise a radio; and clear channel assessment (CCA) logic coupled with the radio to perform guard interval detection on a primary channel of the primary frequency in addition to start of packet detection and energy detection on the primary channel and guard interval detection on a non-primary channel on the primary frequency to determine if a medium is busy in response to entering an active mode from a power-save mode; determine whether the medium is busy based upon the performing; and to output a clear channel assessment indicating that the medium is busy to defer transmissions for a period of time in response to determining that the medium is busy.

In some embodiments, the apparatus may further comprise logic to select the signal on the primary channel. In some embodiments, the CCA logic comprises logic to indicate a clear channel assessment if the medium is not busy. In some embodiments, the CCA logic comprises logic to determine whether a station has transitioned from the power save mode to the active mode; determine whether a network allocation vector is unexpired; and follow start of the packet detection and energy detection and guard interval detection on a non-primary channel of the primary frequency rules if the station did not enter the active mode from the power-saving mode or if there is an indication that the network allocation vector is updated. In some embodiments, the CCA logic comprises guard interval logic to receive a signal on the primary frequency; select the signal on the primary channel; and correlate the signal on the primary channel to detect a guard interval in the signal on the primary channel. In some embodiments, the CCA logic comprises guard interval logic to compare peaks in the correlation to determine if one or more peaks are greater than a threshold correlation value. And in some embodiments of the apparatus, the CCA logic comprises guard interval logic to correlate the signal on the primary channel against a delayed version of the signal on the primary channel.

Another example comprises a system. The system may comprise a medium access control logic to generate a frame for transmission; a receiver comprising clear channel assessment (CCA) logic to perform guard interval detection on a primary channel of the primary frequency in addition to start of packet detection and energy detection on the primary channel and guard interval detection on a non-primary channel of the primary frequency to determine if a medium is busy in response to entering an active mode from a power-save mode; determine whether the medium is busy based upon the performing; and output an indication that the medium is busy to defer transmissions for a period of time in response to detecting a guard interval on the primary channel; and a transmitter to defer transmissions for a period of time in response to determining that the medium is busy.

In some embodiments, the system may further comprise an antenna coupled with the receiver to receive a signal. In some embodiments, the CCA logic comprises logic to indicate a clear channel assessment if the medium is not busy. In some embodiments, the CCA logic comprises logic to determine whether a station has transitioned from the power save mode to the active mode; determine whether a network allocation vector is unexpired; and follow start of the packet detection and energy detection and guard interval detection on a non-primary channel of the primary frequency rules if the station did not enter the active mode from the power-saving mode or if there is an indication that the network allocation vector is updated. In some embodiments, the CCA logic comprises guard interval logic to receive a signal on the primary frequency; select the signal on the primary channel; and correlate the signal on the primary channel to detect a guard interval in the signal on the primary channel. In some embodiments, the CCA logic comprises guard interval logic to compare peaks in the correlation to determine if one or more peaks are greater than a threshold correlation value. And in some embodiments of the apparatus, the CCA logic comprises guard interval logic to correlate the signal on the primary channel against a delayed version of the signal on the primary channel.

Another example comprises a program product. The program product may comprise a medium containing instructions to mitigate collisions between transmissions of devices operating at different bandwidths on a primary frequency of operation. When executed, the instructions cause a receiver to perform operations, the operations comprising: performing guard interval detection on a primary channel on the primary frequency in addition to start of the packet detection and energy detection on the primary channel and guard interval detection on a non-primary channel on the primary frequency to determine if a medium is busy in response to entering an active mode from a power-save mode; determining whether the medium is busy based upon the performing; and outputting a clear channel assessment to defer transmissions for a period of time in response to determining that the medium is busy.

In some embodiments, the program product may further comprise outputting a clear channel assessment indicating that the medium is not busy in response to determining that the medium is not busy. In some embodiments, the program product may further comprise determining whether a station has transitioned from the power save mode to the active mode; determining whether a network allocation vector is unexpired; and following start of packet detection and energy detection and guard interval detection on a non-primary channel of the primary frequency rules if the station did not enter the active mode from the power-saving mode or if there is an indication that the network allocation vector is updated. In many embodiments, the program product may further comprise determining that a network allocation vector is not updated. In several embodiments, performing the guard interval detection on the primary channel of the primary frequency comprises: receiving, by a device, a signal on the primary frequency; selecting the signal on the primary channel; and correlating the signal on the primary channel to detect a guard interval in the signal on the primary channel. In some embodiments, correlating comprises comparing peaks in the correlation to determine if one or more peaks are greater than a threshold correlation value. And, in some embodiments, correlating comprises correlating the signal on the primary channel against a delayed version of the signal on the primary channel.

In some embodiments, some or all of the features described above and in the claims may be implemented in one embodiment. For instance, alternative features may be implemented as alternatives in an embodiment along with logic or selectable preference to determine which alternative to implement. Some embodiments with features that are not mutually exclusive may also include logic or a selectable preference to activate or deactivate one or more of the features. For instance, some features may be selected at the time of manufacture by including or removing a circuit pathway or transistor. Further features may be selected at the time of deployment or after deployment via logic or a selectable preference such as a dipswitch or the like. A user after via a selectable preference such as a software preference, an e-fuse, or the like may select still further features.

A number of embodiments may have one or more advantageous effects. For instance, some embodiments may offer reduced MAC header sizes with respect to standard MAC header sizes. Further embodiments may include one or more advantageous effects such as smaller packet sizes for more efficient transmission, lower power consumption due to less data traffic on both the transmitter and receiver sides of communications, less traffic conflicts, less latency awaiting transmission or receipt of packets, and the like.

Another embodiment is implemented as a program product for implementing systems, apparatuses, and methods described with reference to FIGS. 1-4. Embodiments can take the form of an entirely hardware embodiment, a software embodiment implemented via general purpose hardware such as one or more processors and memory, or an embodiment containing both specific-purpose hardware and software elements. One embodiment is implemented in software or code, which includes but is not limited to firmware, resident software, microcode, or other types of executable instructions.

Furthermore, embodiments can take the form of a computer program product accessible from a machine-accessible, computer-usable, or computer-readable medium providing program code for use by or in connection with a computer, mobile device, or any other instruction execution system. For the purposes of this description, a machine-accessible, computer-usable, or computer-readable medium is any apparatus or article of manufacture that can contain, store, communicate, propagate, or transport the program for use by or in connection with the instruction execution system or apparatus.

The medium may comprise an electronic, magnetic, optical, electromagnetic, or semiconductor system medium. Examples of a machine-accessible, computer-usable, or computer-readable medium include memory such as volatile memory and non-volatile memory. Memory may comprise, e.g., a semiconductor or solid-state memory like flash memory, magnetic tape, a removable computer diskette, a random access memory (RAM), a read-only memory (ROM), a rigid magnetic disk, and/or an optical disk. Current examples of optical disks include compact disk-read only memory (CD-ROM), compact disk-read/write memory (CD-R/W), digital video disk (DVD)-read only memory (DVD-ROM), DVD-random access memory (DVD-RAM), DVD-Recordable memory (DVD-R), and DVD-read/write memory (DVD-R/W).

An instruction execution system suitable for storing and/or executing program code may comprise at least one processor coupled directly or indirectly to memory through a system bus. The memory may comprise local memory employed during actual execution of the code, bulk storage such as dynamic random access memory (DRAM), and cache memories which provide temporary storage of at least some code in order to reduce the number of times code must be retrieved from bulk storage during execution.

Input/output or I/O devices (including but not limited to keyboards, displays, pointing devices, etc.) can be coupled to the instruction execution system either directly or through intervening I/O controllers. Network adapters may also be coupled to the instruction execution system to enable the instruction execution system to become coupled to other instruction execution systems or remote printers or storage devices through intervening private or public networks. Modem, Bluetooth™, Ethernet, Wi-Fi, and WiDi adapter cards are just a few of the currently available types of network adapters.

What is claimed is:

1. A wireless communication station (STA) comprising physical layer (PHY) circuitry and processing elements to:
receive a transmission on a channel of a basic service set (BSS);
determine, in response to receipt of the transmission, whether a network allocation vector (NAV) of the STA indicates idle, which indicates that the channel is idle;
receive an indication of a primary channel and a bandwidth of the primary channel, and, if the NAV indicates idle and the STA determines that the STA has just exited a power save mode such that the STA has not been awake a sufficient time to receive a start of packet (SOP), detect a data portion of a physical layer protocol data unit (PPDU) compatible with a standard of an Institute for Electrical and Electronics Engineers (IEEE) 802.11ah family of standards in the primary channel and in a secondary channel associated with the primary channel; and
refrain from transmitting on the primary channel or secondary channel in response to detection of the data portion in the primary channel or in the secondary channel, wherein the STA is capable to operate within a 2 MHz basic service set (BSS), and the primary channel includes the lower 1 MHz of the 2 MHz BSS operating channel bandwidth.

2. The STA of claim 1, wherein the STA is to detect the data portion of the PPDU based on detection of a guard interval (GI) within the transmission.

3. The STA of claim 2, wherein the STA further includes filtering circuitry to filter a 1 MHz primary channel from the 2 MHz signal, and wherein the processing elements are further to detect the GI in the 1 MHz primary channel.

4. The STA of claim 2, wherein the STA is further to detect the GI in a secondary channel.

5. The STA of claim 1, wherein the STA detects the data portion of the PPDU if the STA has woken from a power save mode within a time duration previous to determining that the NAV associated with the STA indicates that the STA is idle, and the STA refrains from detecting the data portion otherwise.

6. A system comprising:
a transceiver to receive a transmission, addressed to the system, on a channel of a basic service set (BSS); and
processing circuitry and memory to determine, in response to receipt of the transmission addressed to the STA, whether a network allocation vector (NAV) corresponding to the system indicates idle, which indicates that the channel is idle, receive an indication of a primary channel and a bandwidth of the primary channel, and, if the NAV indicates idle and the STA determines that the STA has just exited a power save mode that the STA has not been awake a sufficient time to receive a start of packet (SOP), detect a data portion of a physical layer protocol data unit (PPDU) compatible with a standard of an Institute of Electrical and Electronics Engineers (IEEE) 802.11 ah family of standards in the primary channel and in a secondary channel associated with the primary channel, and refrain from transmitting on the primary channel or secondary channel in response to detection of the data portion in the primary channel or in the secondary channel, wherein the system is capable to operate within a 2 MHz basic service set (BSS), and the primary channel includes the lower 1 MHz of the 2 MHz BSS operating channel bandwidth.

7. The system of claim 6, wherein the transceiver is further capable to be coupled to two or more antennas.

8. The system of claim 6, wherein the system detects the data portion of the PPDU based on detection of a guard interval (GI) within the transmission.

9. The system of claim 8, wherein the system further includes filtering circuitry to filter a 1 MHz primary channel from the 2 MHz signal, and wherein the processing elements are further to detect the GI in the 1 MHz primary channel.

10. The system of claim 8, wherein the system is further to detect the GI in a secondary channel.

11. The system of claim 6, wherein the processing circuitry determines to detect the data portion of the PPDU if the system has woken from a power save mode within a time duration previous to determining that the NAV associated with the system indicates that the system is idle, and the processing circuitry refrains from detecting the data portion otherwise.

12. A non-transitory computer-readable storage medium that stores instructions for execution by one or more processors to perform operations for operating a communication station (STA) in a wireless network, the operation to configure the STA to:
receive a transmission on a channel of a basic service set (BSS);
determine, in response to receipt of the transmission, whether a network allocation vector (NAV) of the STA indicates idle, which indicates that the channel is idle;
receive an indication of a primary channel and a bandwidth of the primary channel, and, if the NAV indicates idle and the STA determines that the STA has just exited a power save mode such that the STA has not been awake a sufficient time to receive a start of packet (SOP), detect a data portion of a physical layer protocol data unit (PPDU) compatible with a standard of an Institute for Electrical and Electronics Engineers (IEEE) 802.11 ah family of standards in the primary channel and in a secondary channel associated with the primary channel; and
refrain from transmitting on the primary channel or secondary channel in response to detection of the data portion in the primary channel or in the secondary channel, wherein the instructions further configure the STA to operate within a 2 MHz basic service set (BSS), and the primary channel includes the lower 1 MHz of the 2 MHz BSS operating channel bandwidth.

13. The non-transitory computer-readable storage medium of claim 12, wherein the instructions further configure the STA to detect the data portion of the PPDU based on detection of a guard interval (GI) within the transmission.

14. The non-transitory computer-readable storage medium of claim 13, wherein the instructions further configure the STA to filter a 1 MHz primary channel from the 2 MHz signal, and wherein the processing elements are further to detect the GI in the 1 MHz primary channel.

15. The non-transitory computer-readable storage medium of claim 13, wherein the instructions further configure the STA to detect the GI in a secondary channel.

16. The non-transitory computer-readable storage medium of claim 12, wherein the instructions further configure the STA to determine whether to detect the data portion of the PPDU based on whether the STA has woken from a power save mode within a time duration previous to determining that the NAV associated with the STA indicates that the STA is idle.

* * * * *